US012569821B2

(12) United States Patent
Berthier

(10) Patent No.: US 12,569,821 B2
(45) Date of Patent: Mar. 10, 2026

(54) MICROCAPSULES COATED WITH A POLYSUCCINIMIDE DERIVATIVE

(71) Applicant: Firmenich SA, Satigny (CH)

(72) Inventor: Damien Berthier, Satigny (CH)

(73) Assignee: FIRMENICH SA, Satigny (CH)

( * ) Notice: Subject to any disclaimer, the term of this patent is extended or adjusted under 35 U.S.C. 154(b) by 605 days.

(21) Appl. No.: 17/906,473

(22) PCT Filed: Mar. 15, 2021

(86) PCT No.: PCT/EP2021/056466
§ 371 (c)(1),
(2) Date: Sep. 15, 2022

(87) PCT Pub. No.: WO2021/185724
PCT Pub. Date: Sep. 23, 2021

(65) Prior Publication Data

US 2023/0134756 A1 May 4, 2023

(30) Foreign Application Priority Data

Mar. 16, 2020 (EP) .................................... 20163294

(51) Int. Cl.

| | |
|---|---|
| ***B01J 13/22*** | (2006.01) |
| ***A61K 8/11*** | (2006.01) |
| ***A61K 8/88*** | (2006.01) |
| ***B01J 13/16*** | (2006.01) |
| ***C11D 3/50*** | (2006.01) |

(52) U.S. Cl.
CPC ................ *B01J 13/22* (2013.01); *A61K 8/11* (2013.01); *A61K 8/88* (2013.01); *B01J 13/16* (2013.01); *C11D 3/505* (2013.01); *A61K 2800/10* (2013.01); *A61K 2800/412* (2013.01)

(58) Field of Classification Search
CPC .. B01J 13/22; B01J 13/16; A61K 8/11; A61K 8/88; A61K 2800/10; A61K 2800/412; C11D 3/505
See application file for complete search history.

(56) References Cited

U.S. PATENT DOCUMENTS

| | | | | |
|---|---|---|---|---|
| 5,175,285 | A * | 12/1992 | Lehmann | A61K 9/2853 548/546 |
| 5,540,927 | A * | 7/1996 | Jason | B01J 13/02 424/408 |
| 6,303,794 | B1 * | 10/2001 | Guth | A61K 8/84 424/70.17 |
| 6,372,880 | B1 | 4/2002 | Shinoda et al. | |
| 2007/0117960 | A1 * | 5/2007 | Kizuka | C08G 73/10 528/310 |
| 2018/0016396 | A1 | 1/2018 | Berthier et al. | |
| 2018/0042825 | A1 * | 2/2018 | Lei | A61K 8/84 |

FOREIGN PATENT DOCUMENTS

| | | | |
|---|---|---|---|
| CN | 104721843 | A | 6/2015 |
| EP | 0 926 185 | A1 | 6/1999 |
| JP | 2000-159888 | A | 6/2000 |
| WO | 2016/131694 | A1 | 8/2016 |

OTHER PUBLICATIONS

Bai X. et al . . . Upconversion luminescence tracking of gene delivery via multifunctional nanocapsules, TALANTA, vol. 150, pp. 118-124 (2015).

* cited by examiner

*Primary Examiner* — Doan T Phan
(74) *Attorney, Agent, or Firm* — Armstrong Teasdale LLP

(57) ABSTRACT

The present invention relates to the field of delivery systems. More specifically, the invention concerns microcapsules coated with a polysuccinimide derivative and can be used in several industries, in particular in the perfumery industry. Perfuming compositions and perfumed consumer products comprising these microcapsules are also objects of the invention.

10 Claims, No Drawings

MICROCAPSULES COATED WITH A POLYSUCCINIMIDE DERIVATIVE

This present application is a U.S. national phase entry under 35 U.S.C. § 371 of PCT Application No. PCT/EP2021/056466, filed Mar. 15, 2021, which claims priority to European Patent Application No. 20163294.0, filed Mar. 16, 2020. The entire contents of these applications are explicitly incorporated herein by this reference.

TECHNICAL FIELD

The present invention relates to the field of delivery systems. More specifically, the invention concerns microcapsules coated with a polysuccinimide derivative that can be used in several industries, in particular in the perfumery industry. Perfuming compositions and perfumed consumer products comprising these microcapsules are also objects of the invention.

BACKGROUND OF THE INVENTION

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner.

In order to be successfully used in consumer products, perfume delivery systems must meet a certain number of criteria. The first requirement concerns stability in aggressive medium. In fact delivery systems may suffer from stability problems, in particular when incorporated into surfactant-based products such as detergents, wherein said systems tend to degrade and lose efficiency in the perfume-retention ability. It is also difficult to have a good stability and a good dispersion of the capsules altogether. The dispersion factor is very important because the aggregation of capsules increases the tendency of the capsule-containing product to phase separate, which represents a real disadvantage. On the other hand, perfume delivery systems must also perform during the actual use of the end-product by the consumer, in particular in terms of odor performance, as the perfume needs to be released when required. Another issue faced for example by the perfumery industry is to provide delivery systems that are well deposited on the substrate for the treatment of which the end product is intended to be used, such as textile, skin, hair or other surfaces, so as to possibly remain on the substrate even after a rinsing step. To address this specific problem, the use of coated capsules has been described in the prior art. For example, cationic capsules are also known to be better dispersed in several applications.

For example, WO 01/41915 discloses a process for the preparation of capsules carrying cationic charges. Such a process is allegedly applicable to a large variety of microcapsules, in particular, polyurethane-polyurea microcapsules are mentioned. After their formation, the capsules are placed in a medium which is favourable for the treatment with cationic polymers. The treatment with cationic polymers is carried out after purification of the basic capsule slurry, in order to eliminate anionic or neutral polymers which were not incorporated in the capsule wall during formation thereof, and other free electrically charged compounds involved in the encapsulation process. In particular, the capsules are diluted, isolated and then re-suspended in water, or even washed to further eliminate anionic compounds. After the purification step, the capsules are agitated vigorously, and the cationic polymers are added. Partially quaternized copolymers of polyvinylpyrrolidones are cited to this purpose, among many other suitable polymers. The described process comprises several steps following the capsule formation, said process being therefore time consuming and not economically profitable.

US 2006/0216509 also discloses a process to render polyurea capsules positively-charged. This process involves the addition, during the wall formation, of polyamines, the capsules thus bearing latent charges, depending on the pH of the medium. Once formed, the capsules are subsequently cationized by acid action or alkylation to bear permanent positive charges. The cationic compounds therefore react with the capsule wall, chemically changing the latter.

WO2009/153695 from the applicant discloses a simplified process for the preparation of polyurea microcapsules bearing permanent positive charges based on the use of a specific stabilizer and which present good deposition on a substrate.

Despite those prior disclosures, there is still a need to improve the ability of perfume delivery systems to deposit on a substrate and to adhere on the substrate for leave-on and rinse-off applications, while performing in terms of perfume release and stability.

The microcapsules of the invention solve this problem as they provide an alternative compared to what was known heretofore such as coated delivery systems.

The present invention provides new microcapsules for delivering an encapsulated perfume and/or other hydrophobic materials, comprising a coating made of a polysuccinimide derivative.

SUMMARY OF THE INVENTION

The present invention solves the above-mentioned problems by providing microcapsules with deposition properties. In particular, the presence of a polysuccinimide derivative is improving the percentage of deposition of microcapsules on a substrate.

A first object of the invention is therefore a core-shell microcapsule slurry comprising at least one microcapsule having a) an oil-based core comprising a hydrophobic material;
b) a polymeric shell; and
c) a coating comprising a polysuccinimide derivative.

A second object of the invention is a core-shell microcapsule having a) an oil-based core comprising a hydrophobic material;
b) a polymeric shell; and
c) a coating comprising a polysuccinimide derivative.

A third object of the invention is a process for the preparation of a microcapsule slurry comprising the following steps:

a) Providing a core-shell microcapsule slurry, and
b) Adding a polysuccinimide derivative to the slurry of step a).

In other aspects, the present invention relates to a consumer product in the form of a shampoo, a shower gel, a rinse-off conditioning composition, a hair-coloration, a liquid detergent or a fabric softener comprising the microcapsule slurry as defined above.

Another object of the invention is a method for improving deposition of microcapsules on a surface, which comprises treating said surface with a perfuming composition or a consumer product as defined in the present invention.

DETAILED DESCRIPTION OF THE INVENTION

Unless stated otherwise, percentages (%) are meant to designate a percentage by weight of a composition.

By "hydrophobic material", it is meant any hydrophobic material—single material or a mixture of materials—which forms a two-phase dispersion when mixed with water.

By "ingredient", it is meant a single compound or a combination of ingredients.

By "perfume or flavour oil", it is meant a single perfuming or flavouring compound or a mixture of several perfuming or flavouring compounds.

By "consumer product" or "end-product" it is meant a manufactured product ready to be distributed, sold and used by a consumer.

A "microcapsule", or the similar, in the present invention it is meant that core-shell microcapsules have a particle size distribution in the micron range (e.g. a mean diameter (Dv(50) comprised between about 1 and 3000 microns) and comprise an external polymer-based shell and an internal continuous oil phase enclosed by the external shell. According to an embodiment, microcapsules have a mean diameter comprised between 1 and 500 microns, preferably from 2 and 200, more preferably between 4 and 100 microns.

By "polyfunctional monomer", it is meant a molecule that, as unit, reacts or binds chemically to form a polymer or supramolecular polymer. The polyfunctional monomer of the invention has at least two functions capable of forming a microcapsule shell.

By "polysuccinimide derivative", it is meant a derivative of a polycondensate of aspartic acid. Preferably, the polysuccinimide derivative is obtained by grafting at least one amine to at least one succinimide repeating unit followed by an optional hydrolysis.

According to a particular embodiment, the polysuccinimide derivative is a cationic polysuccinimide derivative.

By "cationic polysuccinimide derivative", it is meant a polysuccinimide derivative having cationic groups. In other words, according to this embodiment, the polysuccinimide derivative is functionalized with cationic groups.

Preferably, the cationic polysuccinimide derivative is obtained by grafting at least one amine having cationic groups or having groups capable to be cationized to at least one succinimide repeating unit followed by an optional hydrolysis.

The "succinimide repeating unit" is represented by the unit in brackets in the formula below:

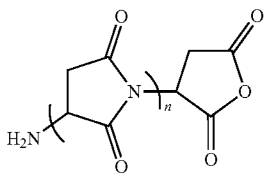

The substitution degree of the polysuccinimide derivative preferably ranges from 5 to 95 mol %, more preferably from 5 to 60 mol %, even more preferably between 5 to 40 mol %.

According to the invention, the terms "amine" or "amino compound" are used indifferently.

For the sake of clarity, by the expression "dispersion" in the present invention it is meant a system in which particles are dispersed in a continuous phase of a different composition and it specifically includes a suspension or an emulsion.

It has been found that core-shell microcapsules with overall good performance namely a good deposition of the active ingredient on different surfaces could be obtained when a polysuccinimide derivative is used as a coating.

Core-Shell Microcapsule

A first object of the invention is a core-shell microcapsule slurry comprising at least one microcapsule having a) an oil-based core comprising a hydrophobic material;

b) a polymeric shell; and c) a coating comprising a polysuccinimide derivative.

According to an embodiment, the polymeric shell comprises a polymerized polyfunctional monomer.

According to an embodiment, the polymeric shell is formed by interfacial polymerisation.

Hydrophobic Material

According to an embodiment, the hydrophobic material is a hydrophobic active ingredient.

According to a preferred embodiment, the active ingredient comprises a perfume oil or a flavour oil. Alternative ingredients which could benefit from being encapsulated could be used either instead of a perfume or flavour, or in combination with a perfume or flavour. Non-limiting examples of such ingredients include a cosmetic, skin caring, malodour counteracting, bactericide, fungicide, pharmaceutical or agrochemical ingredient, a sanitizing agent, an insect repellent or attractant, and mixture thereof.

The nature and type of the insect repellent or attractant that can be present in the hydrophobic internal phase do not warrant a more detailed description here, which in any case would not be exhaustive, the skilled person being able to select them on the basis of its general knowledge and according to the intended use or application.

Examples of such insect repellent or attractant are birch, DEET (N,N-diethyl-m-toluamide), essential oil of the lemon *eucalyptus* (*Corymbia citriodora*) and its active compound p-menthane-3,8-diol (PMD), icaridin (hydroxyethyl isobutyl piperidine carboxylate), Nepelactone, Citronella oil, Neem oil, Bog Myrtle (*Myrica gale*), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

By "perfume oil" (or also "perfume") or "flavour" what is meant here is an ingredient or composition that is a liquid at about 20° C. Said perfume or flavour oil can be a perfuming or flavouring ingredient alone or a mixture of ingredients in the form of a perfuming or flavouring composition. As a "perfuming ingredient" it is meant here a compound, which is used in perfuming preparations or compositions to impart as primary purpose a hedonic effect. In other words such an ingredient, to be considered as being a perfuming one, must be recognized by a person skilled in the art as being able to at least impart or modify in a positive or pleasant way the odor of a composition, and not just as having an odor. The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery.

In particular one may cite perfuming ingredients which are commonly used in perfume formulations, such as:

- Aldehydic ingredients: decanal, dodecanal, 2-methyl-undecanal, 10-undecenal, octanal, nonanal and/or nonenal;
- Aromatic-herbal ingredients: *eucalyptus* oil, camphor, eucalyptol, 5-methyltricyclo[6.2.1.0~2,7~]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;
- Balsamic ingredients: coumarin, ethylvanillin and/or vanillin;
- Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;
- Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino) benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;
- Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl[3-ethyl-2-oxiranyl]acetate and/or diethyl 1,4-cyclohexane dicarboxylate;
- Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;
- Musk ingredients: 1,4-dioxa-5,17-cycloheptadecanedione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{1S)-1-[(1R)-3,3-dimethylcyclohexyl]ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-oneand/or (1S,1'R)-[1-(3',3'-dimethyl-1'-cyclohexyl)ethoxycarbonyl]methyl propanoate,
- Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.$0^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;
- Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

It is also understood that said ingredients may also be compounds known to release in a controlled manner various types of perfuming compounds (also known as properfumes or profragrances). Non-limiting examples of suitable properfume may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-phenylethyl oxo(phenyl)acetate or a mixture thereof.

The perfuming ingredients may be dissolved in a solvent of current use in the perfume industry. The solvent is preferably not an alcohol. Examples of such solvents are Neobee M5, diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Preferred perfuming ingredients are those having a high steric hindrance and in particular those from one of the following groups:

- Group 1: perfuming ingredients comprising a cyclohexane, cyclohexene, cyclohexanone or cyclohexenone ring substituted with at least one linear or branched $C_1$ to $C_4$ alkyl or alkenyl substituent;

Group 2: perfuming ingredients comprising a cyclopentane, cyclopentene, cyclopentanone or cyclopentenone ring substituted with at least one linear or branched $C_4$ to $C_8$ alkyl or alkenyl substituent;

Group 3: perfuming ingredients comprising a phenyl ring or perfuming ingredients comprising a cyclohexane, cyclohexene, cyclohexanone or cyclohexenone ring substituted with at least one linear or branched $C_5$ to $C_8$ alkyl or alkenyl substituent or with at least one phenyl substituent and optionally one or more linear or branched $C_1$ to $C_3$ alkyl or alkenyl substituents;

Group 4: perfuming ingredients comprising at least two fused or linked $C_5$ and/or $C_6$ rings;

Group 5: perfuming ingredients comprising a camphor-like ring structure;

Group 6: perfuming ingredients comprising at least one C7 to C20 ring structure;

Group 7: perfuming ingredients having a log P value above 3.5 and comprising at least one tert-butyl or at least one trichloromethyl substitutent;

Examples of ingredients from each of these groups are:

Group 1: 2,4-dimethyl-3-cyclohexene-1-carbaldehyde (origin: Firmenich SA, Geneva, Switzerland), isocyclocitral, menthone, isomenthone, methyl 2,2-dimethyl-6-methylene-1-cyclohexanecarboxylate (origin: Firmenich SA, Geneva, Switzerland), nerone, terpineol, dihydroterpineol, terpenyl acetate, dihydroterpenyl acetate, dipentene, eucalyptol, hexylate, rose oxide, (S)-1,8-p-menthadiene-7-ol (origin: Firmenich SA, Geneva, Switzerland), 1-p-menthene-4-ol, (1RS,3RS,4SR)-3-p-mentanyl acetate, (1R,2S,4R)-4,6,6-trimethyl-bicyclo[3,1,1]heptan-2-ol, tetrahydro-4-methyl-2-phenyl-2H-pyran (origin: Firmenich SA, Geneva, Switzerland), cyclohexyl acetate, cyclanol acetate, 1,4-cyclohexane diethyldicarboxylate (origin: Firmenich SA, Geneva, Switzerland), (3ARS,6SR,7ASR)-perhydro-3,6-dimethyl-benzo[B]furan-2-one (origin: Firmenich SA, Geneva, Switzerland), ((6R)-perhydro-3,6-dimethyl-benzo[B]furan-2-one (origin: Firmenich SA, Geneva, Switzerland), 2,4,6-trimethyl-4-phenyl-1,3-dioxane, 2,4,6-trimethyl-3-cyclohexene-1-carbaldehyde;

Group 2: (E)-3-methyl-5-(2,2,3-trimethyl-3-cyclopenten-1-yl)-4-penten-2-ol (origin: Givaudan SA, Vernier, Switzerland), (1'R,E)-2-ethyl-4-(2',2',3'-trimethyl-3'-cyclopenten-1'-yl)-2-buten-1-ol (origin: Firmenich SA, Geneva, Switzerland), (1'R,E)-3,3-dimethyl-5-(2',2',3'-trimethyl-3'-cyclopenten-1'-yl)-4-penten-2-ol (origin: Firmenich SA, Geneva, Switzerland), 2-heptylcyclopentanone, methyl-cis-3-oxo-2-pentyl-1-cyclopentane acetate (origin: Firmenich SA, Geneva, Switzerland), 2,2,5-Trimethyl-5-pentyl-1-cyclopentanone (origin: Firmenich SA, Geneva, Switzerland), 3,3-dimethyl-5-(2,2,3-trimethyl-3-cyclopenten-1-yl)-4-penten-2-ol (origin: Firmenich SA, Geneva, Switzerland), 3-methyl-5-(2,2,3-trimethyl-3-cyclopenten-1-yl)-2-pentanol (origin, Givaudan SA, Vernier, Switzerland);

Group 3: damascones, 1-(5,5-dimethyl-1-cyclohexen-1-yl)-4-penten-1-one (origin: Firmenich SA, Geneva, Switzerland), nectalactone ((1'R)-2-[2-(4'-methyl-3'-cyclohexen-1'-yl)propyl]cyclopentanone), alpha-ionone, beta-ionone, damascenone, mixture of 1-(5,5-dimethyl-1-cyclohexen-1-yl)-4-penten-1-one and 1-(3,3-dimethyl-1-cyclohexen-1-yl)-4-penten-1-one (origin: Firmenich SA, Geneva, Switzerland), 1-(2,6,6-trimethyl-1-cyclohexen-1-yl)-2-buten-1-one (origin: Firmenich SA, Geneva, Switzerland), (1S,1'R)-[1-(3',3'-Dimethyl-1'-cyclohexyl)ethoxycarbonyl]methyl propanoate (origin: Firmenich SA, Geneva, Switzerland), 2-tert-butyl-1-cyclohexyl acetate (origin: International Flavors and Fragrances, USA), 1-(2,2,3,6-tetramethyl-cyclohexyl)-3-hexanol (origin: Firmenich SA, Geneva, Switzerland), trans-1-(2,2,6-trimethyl-1-cyclohexyl)-3-hexanol (origin: Firmenich SA, Geneva, Switzerland), (E)-3-methyl-4-(2,6,6-trimethyl-2-cyclohexen-1-yl)-3-buten-2-one, terpenyl isobutyrate, 4-(1,1-dimethylethyl)-1-cyclohexyl acetate (origin: Firmenich SA, Geneva, Switzerland), 8-methoxy-1-p-menthene, (1S,1'R)-2-[1-(3',3'-dimethyl-1'-cyclohexyl)ethoxy]-2-methylpropyl propanoate (origin: Firmenich SA, Geneva, Switzerland), para tert-butylcyclohexanone, menthenethiol, 1-methyl-4-(4-methyl-3-pentenyl)-3-cyclohexene-1-carbaldehyde, allyl cyclohexylpropionate, cyclohexyl salicylate, 2-methoxy-4-methylphenyl methyl carbonate, ethyl 2-methoxy-4-methylphenyl carbonate, 4-ethyl-2-methoxyphenyl methyl carbonate;

Group 4: Methyl cedryl ketone (origin: International Flavors and Fragrances, USA), a mixture of (1RS,2SR,6RS,7RS,8SR)-tricyclo[5.2.1.0˜2,6˜]dec-3-en-8-yl 2-methylpropanoate and (1RS,2SR,6RS,7RS,8SR)-tricyclo[5.2.1.0˜2,6˜]dec-4-en-8-yl 2-methylpropanoate, vetyverol, vetyverone, 1-(octahydro-2,3,8,8-tetramethyl-2-naphtalenyl)-1-ethanone (origin: International Flavors and Fragrances, USA), (5RS,9RS,10SR)-2,6,9,10-tetramethyl-1-oxaspiro[4.5]deca-3,6-diene and the (5RS,9SR,10RS) isomer, 6-ethyl-2,10,10-trimethyl-1-oxaspiro[4.5]deca-3,6-diene, 1,2,3,5,6,7-hexahydro-1,1,2,3,3-pentamethyl-4-indenone (origin: International Flavors and Fragrances, USA), a mixture of 3-(3,3-dimethyl-5-indanyl)propanal and 3-(1,1-dimethyl-5-indanyl)propanal (origin: Firmenich SA, Geneva, Switzerland), 3',4-dimethyl-tricyclo[6.2.1.0(2,7)]undec-4-ene-9-spiro-2'-oxirane (origin: Firmenich SA, Geneva, Switzerland), 9/10-ethyldiene-3-oxatricyclo[6.2.1.0(2,7)]undecane, (perhydro-5,5,8A-trimethyl-2-naphthalenyl acetate (origin: Firmenich SA, Geneva, Switzerland), octalynol, (dodecahydro-3a,6,6,9a-tetramethyl-naphtho[2,1-b]furan, origin: Firmenich SA, Geneva, Switzerland), tricyclo[5.2.1.0(2,6)]dec-3-en-8-yl acetate and tricyclo[5.2.1.0(2,6)]dec-4-en-8-yl acetate as well as tricyclo[5.2.1.0(2,6)]dec-3-en-8-yl propanoate and tricyclo[5.2.1.0(2,6)]dec-4-en-8-yl propanoate, (+)-(1S,2S,3S)-2,6,6-trimethyl-bicyclo[3.1.1]heptane-3-spiro-2'-cyclohexen-4'-one;

Group 5: camphor, borneol, isobornyl acetate, 8-isopropyl-6-methyl-bicyclo[2.2.2]oct-5-ene-2-carbaldehyde, pinene, camphene, 8-methoxycedrane, (8-methoxy-2,6,6,8-tetramethyl-tricyclo[5.3.1.0(1,5)]undecane (origin: Firmenich SA, Geneva, Switzerland), cedrene, cedrenol, cedrol, mixture of 9-ethylidene-3-oxatricyclo[6.2.1.0(2,7)]undecan-4-one and 10-ethylidene-3-oxatricyclo[6.2.1.0(2,7)]undecan-4-one (origin: Firmenich SA, Geneva, Switzerland), 3-methoxy-7,7-dimethyl-10-methylene-bicyclo[4.3.1]decane (origin: Firmenich SA, Geneva, Switzerland);

Group 6: (trimethyl-13-oxabicyclo-[10.1.0]-trideca-4,8-diene (origin: Firmenich SA, Geneva, Switzerland), Ambrettolide LG ((E)-9-hexadecen-16-olide, origin: Firmenich SA, Geneva, Switzerland), pentadecenolide (origin: Firmenich SA, Geneva, Switzerland), muscenone (3-methyl-(4/5)-cyclopentadecenone, origin: Firmenich SA, Geneva, Switzerland), 3-methylcyclopentadecanone (origin: Firmenich SA, Geneva, Switzerland), pentadecanolide (origin: Firmenich SA, Geneva, Switzerland), cyclopentadecanone (origin: Firmenich SA, Geneva, Switzerland), 1-ethoxyethoxy) cyclododecane (origin: Firmenich SA, Geneva, Switzerland), 1,4-dioxacycloheptadecane-5,17-dione, 4,8-cyclododecadien-1-one;

Group 7: (+−)-2-methyl-3-[4-(2-methyl-2-propanyl)phenyl]propanal (origin: Givaudan SA, Vernier, Switzerland), 2,2,2-trichloro-1-phenylethyl acetate.

Preferably, the perfume comprises at least 30%, preferably at least 50%, more preferably at least 60% of ingredients selected from Groups 1 to 7, as defined above. More preferably said perfume comprises at least 30%, preferably at least 50% of ingredients from Groups 3 to 7, as defined above. Most preferably said perfume comprises at least 30%, preferably at least 50% of ingredients from Groups 3, 4, 6 or 7, as defined above.

According to another preferred embodiment, the perfume comprises at least 30%, preferably at least 50%, more preferably at least 60% of ingredients having a log P above 3, preferably above 3.5 and even more preferably above 3.75.

Preferably, the perfume used in the invention contains less than 10% of its own weight of primary alcohols, less than 15% of its own weight of secondary alcohols and less than 20% of its own weight of tertiary alcohols. Advantageously, the perfume used in the invention does not contain any primary alcohols and contains less than 15% of secondary and tertiary alcohols.

According to an embodiment, the oil phase (or the oil-based core) comprises:

25-100 wt % of a perfume oil comprising at least 15 wt % of high impact perfume raw materials having a Log T<−4, and 0-75 wt % of a density balancing material having a density greater than 1.07 g/cm$^3$.

The nature of high impact perfume raw materials having a Log T<−4 and density balancing material having a density greater than 1.07 g/cm$^3$ are described in WO2018115250, the content of which are included by reference.

According to a particular embodiment, the hydrophobic material is free of any active ingredient (such as perfume). According to this particular embodiment, it comprises, preferably consists of hydrophobic solvents, preferably chosen in the group consisting of isopropyl myristate, tryglycerides (e.g. Neobee® MCT oil, vegetable oils), D-limonene, silicone oil, mineral oil, and mixtures thereof with optionally hydrophilic solvents preferably chosen in the group consisting of 1,4 butanediol, benzyl alcohol, triethyl citrate, triacetin, benzyl acetate, ethyl acetate, propylene glycol (1,2-propanediol), 1,3-Propanediol, dipropylene glycol, glycerol, glycol ethers and mixtures thereof.

Polymeric Shell

The nature of the polymeric shell of the microcapsule can vary.

According to a particular embodiment, the polymeric shell comprises a material selected from the group consisting of polyurea, polyurethane, polyamide, polyester, polyacrylate, polysiloxane, polycarbonate, polysulfonamide, polymers of urea and formaldehyde, melamine and formaldehyde, melamine and urea, or melamine and glyoxal and mixtures thereof.

According to a particular embodiment, the polymeric shell comprises a material chosen from the group consisting of polyurea and/or polyurethane.

The material encapsulating the hydrophobic material composition can be microcapsules which have been widely described in the prior art.

As non-limiting examples, the shell can be aminoplast-based, polyurea-based or polyurethane-based. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an aspect, the shell comprises an aminoplast copolymer, such as melamine-formaldehyde or urea-formaldehyde or cross-linked melamine formaldehyde or melamine glyoxal.

According to another aspect the shell is polyurea-based made from, for example but not limited to isocyanate-based monomers and amine-containing crosslinkers such as guanidine carbonate and/or guanazole. Certain polyurea microcapsules comprise a polyurea wall which is the reaction product of the polymerisation between at least one polyisocyanate comprising at least two isocyanate functional groups and at least one reactant selected from the group consisting of an amine (for example a water-soluble guanidine salt and guanidine); a colloidal stabilizer or emulsifier; and an encapsulated perfume. However, the use of an amine can be omitted.

According to a particular aspect, the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). According to another aspect, the emulsifier is an anionic or amphiphilic biopolymer, which may be, in one aspect, chosen from the group consisting of gum Arabic, soy protein, gelatin, sodium caseinate and mixtures thereof. According to another aspect, the shell is polyurethane-based made from, for example but not limited to polyisocyanate and polyols, polyamide, polyester, etc.

According to another embodiment, the microcapsules have a polymeric shell resulting from complex coacervation wherein the shell is possibly cross-linked such as described in WO2014044840.

According to another embodiment, the microcapsules have a shell as described in WO2019243426.

The preparation of an aqueous dispersion/slurry of core-shell microcapsules is well known by a skilled person in the art. In one aspect, the microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Missouri U.S.A.), Cytec Industries (West Paterson, New Jersey U.S.A.), Sigma-Aldrich (St. Louis, Missouri U.S.A.).

According to one aspect, the microcapsule is a one-shell aminoplast core-shell microcapsule obtainable by a process comprising the steps of:

1) admixing a perfume oil with at least a polyisocyanate having at least two isocyanate functional groups to form an oil phase;
2) dispersing or dissolving into water an aminoplast resin and optionally a stabilizer to form a water phase;
3) preparing an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain the dried core-shell microcapsule.

According to one aspect, the core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together:
   a. a polyamine component in the form of melamine or of a mixture of melamine and at least one $C_1$-$C_4$ compound comprising two NH2 functional groups;
   b. an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c. a protic acid catalyst;
2) preparing an oil-in-water dispersion, wherein the droplet size is comprised between 1 and 600 microns, and comprising:
   a. an oil;
   b. a water medium:
   c. at least an oligomeric composition as obtained in step 1;
   d. at least a cross-linker selected amongst:
      i. $C_4$-$C_{12}$ aromatic or aliphatic di- or tri-isocyanates and their biurets, triurets, trimmers, trimethylol propane-adduct and mixtures thereof; and/or
      ii. a di- or tri-oxiran compounds of formula:

A-(oxiran-2-ylmethyl)$_n$ wherein $_n$ stands for 2 or 3 and 1 represents a $C_2$-$C_6$ group optionally comprising from 2 to 6 nitrogen and/or oxygen atoms;

e. optionally a $C_1$-$C_4$ compounds comprising two $NH_2$ functional groups;
3) Heating the dispersion; and
4) Cooling the dispersion.

The above process is described in more details in International Patent Application Publication No. WO 2013/068255.

According to another aspect, the shell of the microcapsule is polyurea- or polyurethane-based. Examples of processes for the preparation of polyurea and polyureathane-based microcapsule slurry are for instance described in International Patent Application Publication No. WO2007/004166, European Patent Application Publication No. EP 2300146, and European Patent Application Publication No. EP25799. Typically a process for the preparation of polyurea or polyurethane-based microcapsule slurry include the following steps:

a) Dissolving at least one polyisocyanate having at least two isocyanate groups in an oil to form an oil phase;
b) Preparing an aqueous solution of an emulsifier or colloidal stabilizer to form a water phase;
c) Adding the oil phase to the water phase to form an oil-in-water dispersion, wherein the mean droplet size is comprised between 1 and 500 μm, preferably between 5 and 50 μm; and
d) Applying conditions sufficient to induce interfacial polymerisation and form microcapsules in form of a slurry.

Polysuccinimide Derivative Coating

The polysuccinimide derivative used in the invention is preferably obtained by grafting at least one amine to at least one succinimide repeating unit.

According to a particular embodiment, the polysuccinimide derivative is a cationic polysuccinimide derivative.

According to an embodiment, the amine has at least one cationic group.

According to a particular embodiment, the polysuccinimide derivative is obtained by grafting two amines to the polysuccinimide. According to a particular embodiment, the two amines are added successively.

Once the at least amine is grafted on the polysuccinimide, said resulting polysuccinimide derivative can be subjected to an hydrolysis before introducing it in water to form the aqueous phase and/or when introducing in water to form the aqueous phase.

According to a particular embodiment, the hydrolysis step takes place when the polysuccinimide is in contact with water to form the aqueous phase.

Any functional amine can be grafted, preferably monofunctional amine or amino acid to prevent cross-linking.

According to an embodiment, functional mono or polyamines that can be grafted on succinimide repeating unit have the following structures:

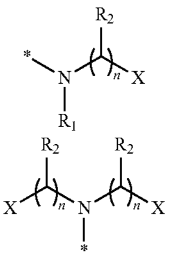

$R_1$, $R_2$ = H or Me, Et

X = Me, OH, $NH_2$, SH, $N^+(R_1)_3$, $SO_3H$, $SO_3Na$, $CO_2H$, $CO_2Na$ n = 2 - 17

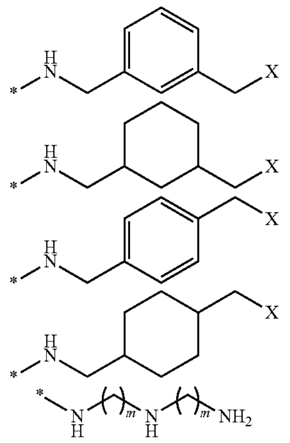

m = 2 - 4

-continued

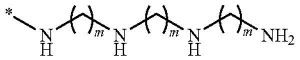

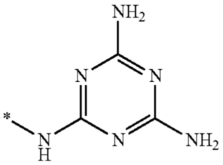

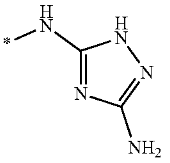

According to a particular embodiment, in the above formula, $X{=}NH_2$ or $X{=}N^+(R_1)^3$.

Amino acids can also be grafted on the succinimide repeating units. Amino acids that can be used in the present invention have the following structures:

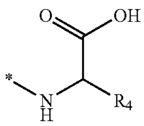

Where

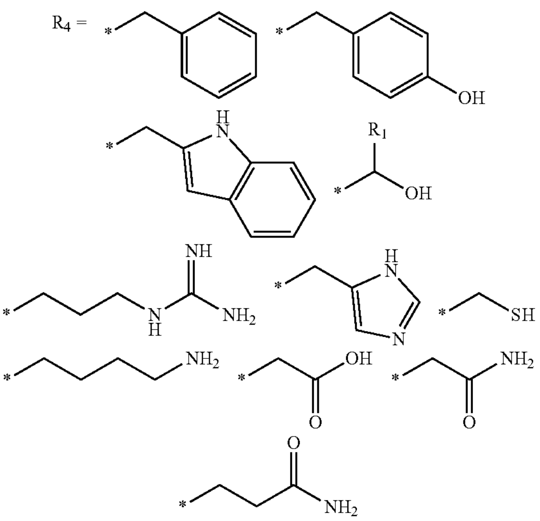

According to a particular embodiment, amino acids have the following structures.

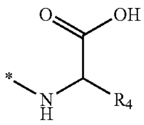

Where

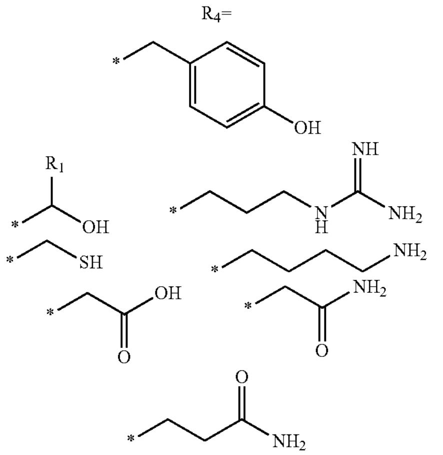

According to another particular embodiment, amino acids have the following structures.

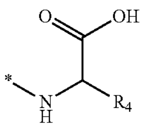

Where $R_4$=

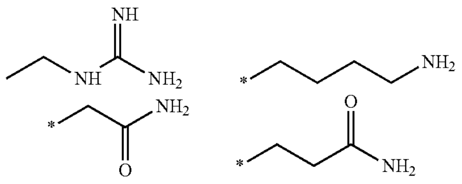

According to a particular embodiment, catechol groups can be grafted on the succinimide repeating units.

According to a particular embodiment, the amine is chosen in the group consisting of glycidyltrimethylammonium chloride, N,N-Dimethyltrimethylenediamine (DMAPA), 1-dimethylamino-2-propylamine, (2-Aminoethyl)trimethylammonium chloride hydrochloride, (5-bromopentyl)trimethylammonium bromide, (2-Chloroethyl) trimethylammonium chloride, Bromopropyl) trimethylammonium bromide, N,N-Bis(3-aminopropyl) methylamine (DAMDPA), ethanolamine, cystamine and mixtures thereof.

According to a particular embodiment, the polysuccinimide is modified with at least two amines, preferably chosen in the group consisting of N,N-Dimethyltrimethylenediamine (DMAPA), N,N-Bis(3-aminopropyl)methylamine (DAMDPA).

According to a particular embodiment, the molar ratio between N,N-Bis(3-aminopropyl)methylamine (DAMDPA) and the polysuccinimide (PSI) is comprised between 0.1 to 0.01, preferably between 0.08 and 0.02.

According to a particular embodiment, the molar ratio between N,N-Dimethyltrimethylenediamine (DMAPA) and the polysuccinimide (PSI) is comprised between 1 to 0.01, preferably between 0.08 and 0.1.

According to a particular embodiment, the molar ratio between N,N-ethanolamine and the polysuccinimide (PSI) is comprised between 1 to 0.01, preferably between 0.08 and 0.1.

According to another embodiment, the amine is chosen in the group consisting of n-alkyl amine, hydroxyl alkyl amine, M-type Jeffamine® (polyoxyalkylenepolyamine), amino acids, dopamine, DOPA and mixtures thereof.

According to a particular embodiment, the amine is chosen in the group consisting of 1-Dodecylamine (DDA), 1-decylamine, dopamine, 2-aminoethan-1-ol, 3-amino-propan-1-ol, 6-amino-hexan-1-ol and mixtures thereof.

According to an embodiment, the amine is chosen in the group consisting of n-alkyl amine, hydroxyl alkyl amine, M-type Jeffamine®, amino acids, dopamine, DOPA and mixtures thereof.

According to a particular embodiment, the amine is chosen in the group consisting of 1-Dodecylamine (DDA), 1-decylamine, dopamine, 2-aminoethan-1-ol, 3-amino-propan-1-ol, 6-amino-hexan-1-ol and mixtures thereof.

According to a particular embodiment, the polysuccinimide is modified with at least two amines, preferably chosen in the group consisting of 1-Dodecylamine (DDA), 1-decylamine, dopamine, 2-aminoethan-1-ol, 3-amino-propan-1-ol and 6-amino-hexan-1-ol.

According to an embodiment, the polysuccinimide derivative is preferably chosen in the group consisting of polysuccinimide-co-poly(n-ethylaspartamide), polysuccinimide-co-poly(n-butylaspartamide), polysuccinimide-co-poly(n-hexylaspartamide), polysuccinimide-co-poly(n-dodecylaspartamide), polysuccinimide-co-poly(n-dodecylaspartamide)-co-poly(3,4-dihydroxybenzylaspartamide), and mixtures thereof.

It should be noted that when the above compounds are dissolved in water, they form respectively compounds chosen in the group consisting in poly(aspartic acid)-co-poly(n-ethylaspartamide), poly(aspartic acid)-co-poly(n-butylaspartamide), poly(aspartic acid)-co-poly(n-hexylaspartamide), poly(aspartic acid)-co-poly(n-dodecylaspartamide), poly(aspartic acid)-co-poly(n-dodecylaspartamide)-co-poly(3,4-dihydroxybenzylaspartamide) and mixtures thereof.

According to an embodiment, the polysuccinimide derivative is obtained by the following process:

a) polycondensation of aspartic acid in the presence of acid catalyst to obtain a polysuccinimide;
b) addition of at least one amine, preferably an amine having cationic group, to the polysuccinimide of step a) to obtain a polysuccinimide derivative;
c) optionally, hydrolysis of polysuccinimide derivative in water.

According to a particular embodiment, the acid catalyst is phosphoric acid or adipic acid.

According to a particular embodiment, the polysuccinimide derivative is a polysuccinimide-co-poly(n-dodecylaspartamide) and is obtained by the following process:

a) polycondensation of aspartic acid in the presence of acid catalyst to obtain a polysuccinimide;
b) addition of n-dodecyl amine to the polysuccinimide of step a) to obtain a polysuccinimide derivative;
c) optionally, hydrolysis of polysuccinimide derivative in water.

According to a particular embodiment, the polysuccinimide derivative is a polysuccinimide-co-poly(n-dodecylaspartamide)-co-poly(3,4-dihydroxybenzylaspartamide) and is obtained by the following process:

a) polycondensation of aspartic acid in the presence of acid catalyst to obtain a polysuccinimide;
b) addition of n-dodecyl amine to the polysuccinimide of step a) to obtain poly(succinimide-co-n-dodecylaspartamide);
c) addition of dopamine on compound obtained in step b) to obtain a polysuccinimide derivative; and
d) optionally, hydrolysis of polysuccinimide derivative in water.

According to an embodiment, when the polysuccinimide derivative is a polysuccinimide-co-poly(n-dodecylaspartamide)-co-poly(3,4-dihydroxybenzylaspartamide), the molar ratio between dopamine and 1-dodecylamine is comprised between 0.5 and 8, preferably between 1 and 4.

According to a particular embodiment, the polysuccinimide derivative is a cationic polyaspartamide-co-polysuccinimide-co-poly(aspartic acid).

According to an embodiment, the polysuccinimide derivative is chosen in the group consisting of PSI-co-DAMDPA-g-DMAPA-co-Mel, PSI-g-DMAPA-co-Mel and PSI-co-AD-g-DMAPA-co-Mel.

The polysuccinimide can also be obtained by reactive extrusion, preferably in the presence of aliphatic diacids, such for example adipic acid. When prepared by extrusion, the temperature of the extruder is preferably comprised between 30 and 250° C., preferably between 80 and 210° C. Polycondensation of adipic acid and aspartic acid should take place at a temperature above 150° C. in the extruder.

When adipic acid is used, the molar ratio between aspartic acid and adipic acid is between 20/1 to 5/1, preferably between 15/1 to 7/1.

A minimum of 5 mol % of adipic acid is needed, at least 6.6 mol % to obtain a good conveying in the extruder, more preferably 10 to 15 mol %.

According to an embodiment, the cationic polysuccinimide derivative (compound 1) is obtained by the following process.

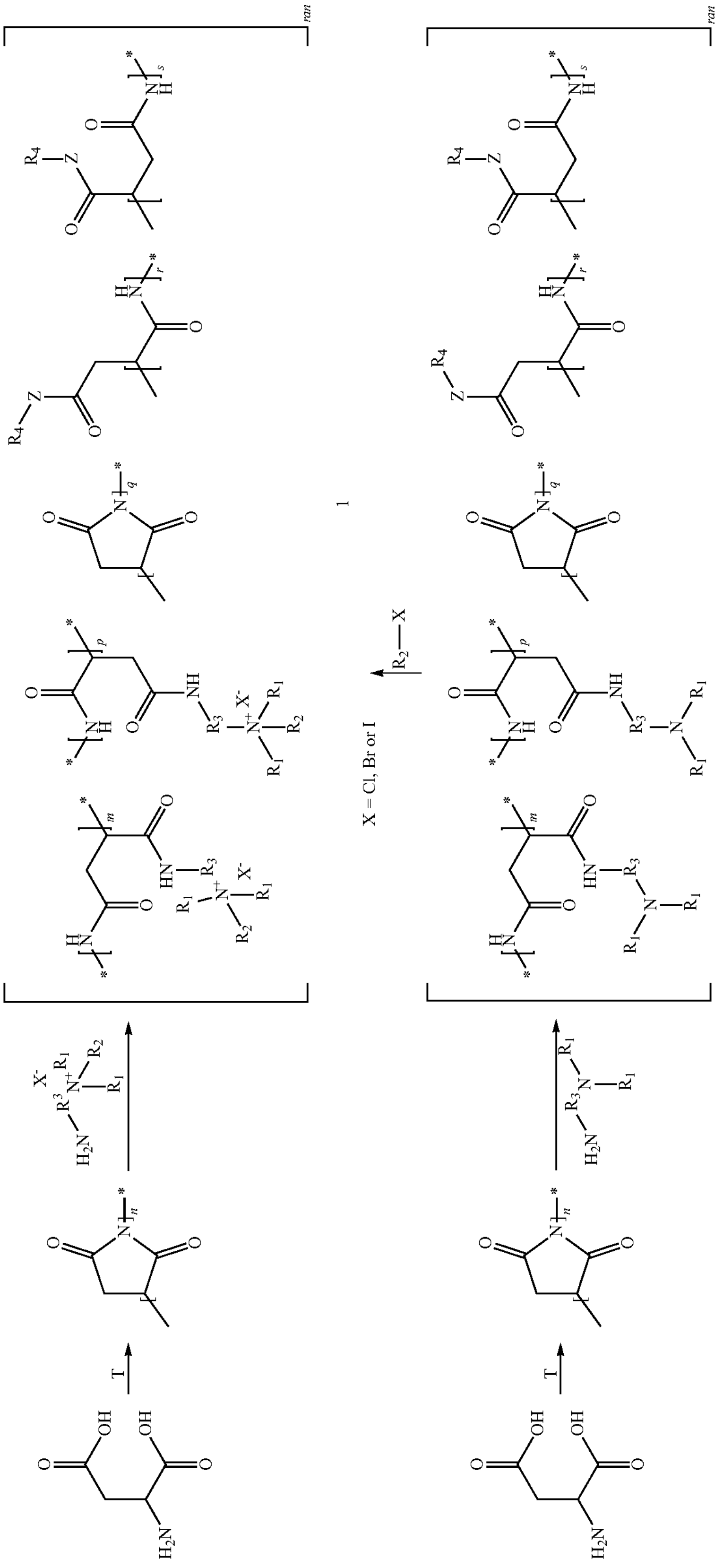
1
$R_1$ = Me, Et, n-Pro, n-Bu or t-Bu
$R_2$ = H, Me, Et, n-Pro, n-Bu or t-Bu
$R_3$ = —$(CH_2)n$—
n = 2-18
Z = O or NH
$R_4$ = H, Na or $R_5$
$R_5$ = $(CH_2)n$—$R_6$
$R_6$ = H, OH or SH According to another embodiment, the cationic polysuccinimide derivative (compound 2) is obtained by the following process.

xyloglucan, guar gum, hydroxypropyl guar, hydroxypropyl cellulose and hydroxypropyl methyl cellulose, pectin and mixtures thereof.

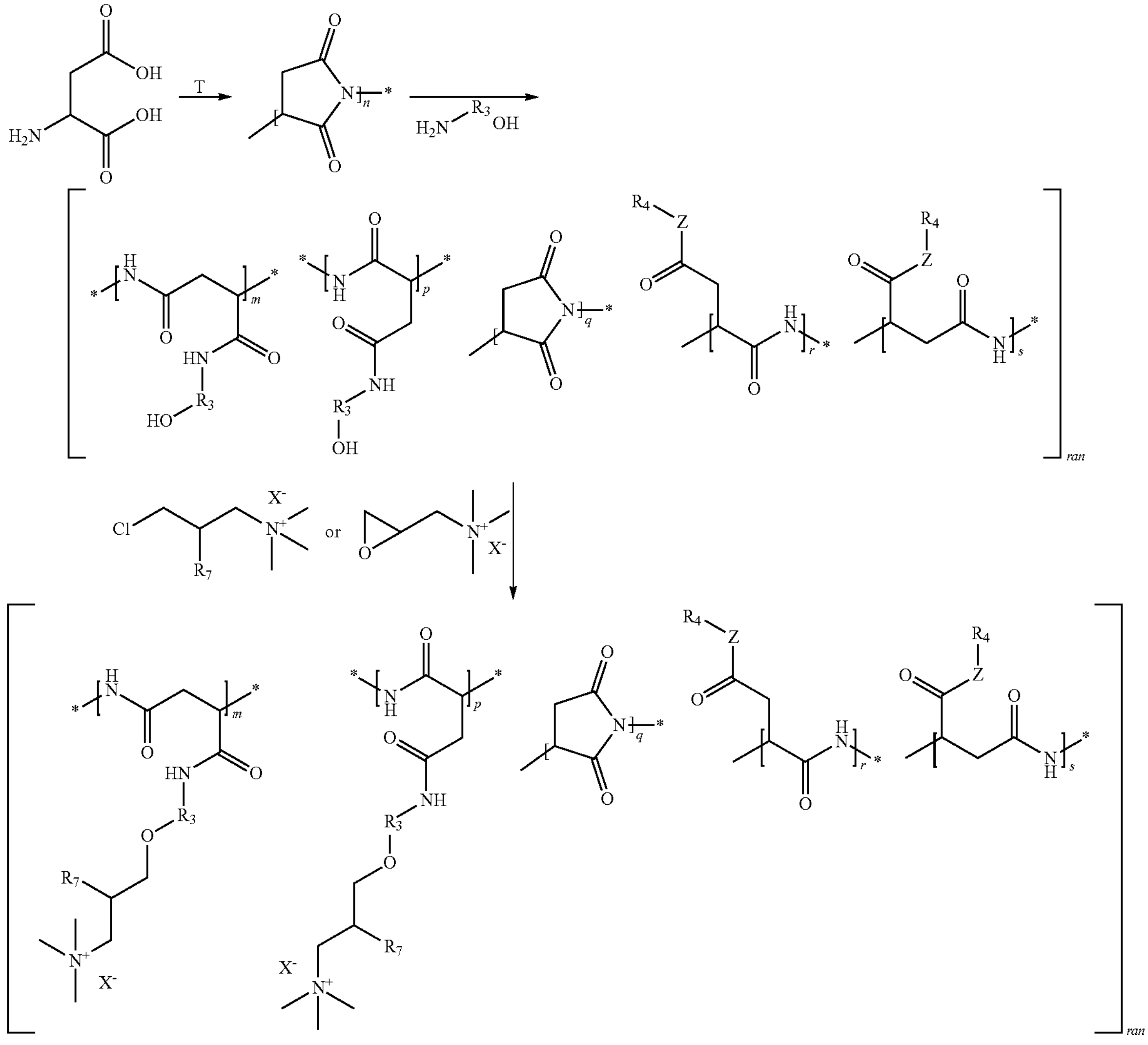

2

It should be understood that, according to the invention the polymeric shell is not formed from the reaction between a polyfunctional monomer (polymeric material) and the polysuccinimide derivative. Indeed, according to the invention, the polysuccinimide derivative is not used as an emulsifier but is used as a coating.

According to a particular embodiment, the polymeric shell does not comprise the polysuccinimide derivative.

The polysuccinimide derivative is preferably used in an amount comprised between 0.1 and 5% by weight, more preferably between 0.5 and 2.5% by weight, relative to the total weight of the slurry.

The polysuccinimide derivative of the present invention can be used alone or in combination with other well-known polymers (a polysaccharide and/or a cationic polymer).

Polysaccharide polymers are well known to a person skilled in the art. Preferred non-ionic polysaccharides are selected from the group consisting of locust bean gum, Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 1.5M Dalton. According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, *cassia* hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, *cassia* hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

Process for Preparing a Core-Shell Microcapsules Slurry

Another object of the invention is a process for the preparation of a microcapsule slurry comprising the following steps:

a) Providing a core-shell microcapsule slurry, and
b) Adding a polysuccinimide derivative to the slurry of step a).

The process for preparing a core-shell microcapsule slurry is well-known from the person skilled in the art and have been disclosed above.

The polysuccinimide derivative is preferably used in an amount comprised between 0.1 and 5% by weight, more preferably between 0.5 and 2.5% by weight, relative to the total weight of the slurry.

According to another aspect, the present invention discloses a process for preparing the microcapsule slurry as defined above, wherein it comprises the steps of:

a) Preparing an oil phase comprising a hydrophobic material to form an oil phase;
b) Preparing an aqueous solution comprising optionally an emulsifier to form a water phase;
c) Adding the oil phase to the water phase to form an oil-in-water dispersion; and
d) Performing a curing step to form core-shell microcapsule in the form of a slurry;
wherein a polyfunctional monomer is added in the oil phase and/or the water phase and
wherein a polysuccinimide derivative is added in step d) or after step d) is completed.

According to an embodiment, the polysuccinimide derivative is not added in step b).

According to an embodiment, the polyfunctional monomer is chosen in the group consisting of at least one polyisocyanate, poly maleic anhydride, poly acid chloride, polyepoxide, acrylate monomers, polyalkoxysilane, melamine-based resin and mixtures thereof.

The polyfunctional monomer used in the process according to the invention is present in amounts representing from 0.1 to 15%, preferably from 0.5 to 10% and more preferably from 0.8 to 6%, and even more preferably between 1 and 3% by weight of the oil phase and/or the water phase.

According to an embodiment, the polyfunctional monomer is added in the oil phase.

The previous embodiment is particularly suitable, when the polyfunctional monomer is soluble in oil (for example when polyisocyanate is used as a polyfunctional monomer).

According to an embodiment, the polyfunctional monomer is added in the water phase.

The previous embodiment is particularly suitable, when the polyfunctional monomer is soluble in water (for example when a melamine resin is used as a polyfunctional monomer).

According to an embodiment, a first polyfunctional monomer is added in the water phase (for example a melanin resin) and a second polyfunctional monomer (for example a polyisocyanate) is added in the oil phase.

The emulsifier can be an ionic or non-ionic surfactant or a colloidal stabilizer. As non-limiting examples, non-ionic polymers include polyvinyl alcohol, cellulose derivatives such hydroxyethyl cellulose, polyethylene oxide, co-polymers of polyethylene oxide and polyethylene or polypropylene oxide, co-polymers alkyl acrylates and N-vinypyrrolidone, and non-ionic polysaccharide. Ionic polymers include co-polymers of acrylamide and acrylic acid, acid anionic surfactant (such as sodium dodecyl sulfate), acrylic co-polymers bearing a sulfonate group, and co-polymers of vinyl ethers and maleic anhydride, and ionic polysaccharide.

The curing step allows ending up with microcapsules in the form of a slurry. According to a preferred embodiment, said step is performed at a temperature comprised between 60 and 80° C., possibly under pressure, for 1 to 4 hours. More preferably it is performed at between 50 and 90° C. for between 30 minutes and 4 hours.

Perfuming Composition/Consumer Products

Another object of the present invention is a perfuming composition comprising:

(i) microcapsules as defined above, wherein the oil comprises a perfume;
(ii) at least one ingredient selected from the group consisting of a perfumery carrier, a perfumery co-ingredient and mixtures thereof;
(iii) optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to at least impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds. Co-ingredients may be chosen in the group consisting of 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-phenylethyl oxo(phenyl)acetate and a mixture thereof.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsules as defined above.

The invention's microcapsules can advantageously be used in many application fields and used in consumer products. Microcapsules can be used in liquid form applicable to liquid consumer products as well as in powder form, applicable to powder consumer products.

Another object of the invention is a consumer product comprising:

a) a personal care active base, and b) microcapsules as defined above or the perfuming composition as defined above, wherein the consumer product is in the form of a personal care composition.

Personal care active base in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

The personal care composition is preferably chosen in the group consisting of a hair-care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product) or a fine fragrance product (e.g. Eau de Toilette—EdT).

Another object of the invention is a consumer product comprising:

a) a home care or a fabric care active base, and b) microcapsules as defined above or the perfuming composition as defined above, wherein the consumer product is in the form of a home care or a fabric care composition.

Home care or fabric care bases in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature. The home or fabric care composition is preferably chosen in the group consisting fabric softener, liquid detergent, powder detergent, liquid scent booster, solid scent booster (e.g. using PEG/urea or salts).

According to a particular embodiment, the consumer product as defined above is liquid and comprises:

a) from 2 to 65% by weight, relative to the total weight of the consumer product, of at least one surfactant;

b) water or a water-miscible hydrophilic organic solvent; and c) microcapsule slurry as defined above, d) optionally non-encapsulated perfume.

According to a particular embodiment, the consumer product as defined above is in a powder form and comprises:

(a) from 2 to 65% by weight, relative to the total weight of the consumer product, of at least one surfactant;

(b) microcapsule powder as defined above.

(c) optionally perfume powder that is different from the microcapsules defined above.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

In particular a liquid consumer product comprising:

a) from 2 to 65% by weight, relative to the total weight of the consumer product, of at least one surfactant;

b) water or a water-miscible hydrophilic organic solvent; and c) a perfuming composition as defined above is another object of the invention.

Also a powder consumer product comprising (a) from 2 to 65% by weight, relative to the total weight of the consumer product, of at least one surfactant; and (b) a perfuming composition as defined above is part of the invention.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as “base”, together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumed consumer product can be a perfume, such as a fine perfume, a cologne, an after-shave lotion, a body-splash; a fabric care product, such as a liquid or solid detergent, tablets and pods, a fabric softener, a dryer sheet, a fabric refresher, an ironing water, or a bleach; a personal-care product, such as a hair-care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener, a “ready to use” powdered air freshener, a powdered air freshener; or a home care product, such all-purpose cleaners, liquid or powder or tablet dishwashing products, toilet cleaners or products for cleaning various surfaces, for example sprays & wipes intended for the treatment/refreshment of textiles or hard surfaces (floors, tiles, stone-floors etc.); a hygiene product such as sanitary napkins, diapers, toilet paper.

According to a particular embodiment, the perfumed consumer product is a fine perfume, a splash or eau de perfume, a cologne, a shave or after-shave lotion, a liquid or solid detergent, a mono or multi chamber unidose detergent, a fabric softener, a fabric refresher, liquid or solid scent-boosters (e.g. using PEG/urea or salts), a dryer sheet, an ironing water, a paper, a bleach, a carpet cleaners, curtain-care products, a shampoo, a coloring preparation, a color care product, a hair shaping product, a dental care product, a disinfectant, an intimate care product, a hair spray, a hair conditioning product, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a “ready to use” powdered air freshener, a powdered air freshener, a mold remover, furnisher care, wipe, a dish detergent or hard-surface detergent, a leather care product, a car care product.

According to a particular embodiment, the perfumed consumer product is a liquid or solid detergent, a fabric softener, liquid or solid scent-boosters (e.g. using PEG/urea or salts), a shampoo, a shower gel, a hair conditioning product (e.g. leave on or rinse-off), a deodorant or antiperspirant.

Preferably, the consumer product comprises from 0.05 to 15 wt %, preferably 0.1 to 15 wt %, more preferably between 0.2 and 5 wt % of the microcapsules of the present invention, these percentages being defined by weight relative to the total weight of the consumer product. Of course the above concentrations may be adapted according to the benefit effect desired in each product.

For liquid consumer product mentioned below, by “active base”, it should be understood that the active base includes active materials (typically including surfactants) and water.

For solid consumer product mention below, by “active base”, it should be understood that the active base includes active materials (typically including surfactants) and auxiliary agents (such as bleaching agents, buffering agent; builders; soil release or soil suspension polymers; granulated enzyme particles, corrosion inhibitors, antifoaming, sud suppressing agents; dyes, fillers, and mixtures thereof).

Fabric Softener

An object of the invention is a consumer product in the form of a fabric softener composition comprising:

- a fabric softener active base; preferably comprising at least one active material chosen in the group consisting of dialkyl quaternary ammonium salts, dialkyl ester quaternary ammonium salts (esterquats), Hamburg esterquat (HEQ), TEAQ (triethanolamine quat), silicones and mixtures thereof, the active base being used preferably in an amount comprised between 85 and 99.95% by weight based on the total weight of the composition,
- a microcapsule slurry as defined above, preferably in an amount comprised between 0.05 to 15 wt %, more preferably between 0.1 and 5 wt % by weight based on the total weight of the composition,
- optionally free perfume oil.

Liquid Detergent

An object of the invention is a consumer product in the form of a liquid detergent composition comprising:

- a liquid detergent active base; preferably comprising at least one active material chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, the active base being used preferably in an amount comprised between 85 and 99.95% by weight based on the total weight of the composition,
- a microcapsule slurry as defined above, preferably in an amount comprised between 0.05 to 15 wt %, more preferably between 0.1 and 5 wt % by weight based on the total weight of the composition,
- optionally free perfume oil.

Solid Detergent

An object of the invention is a consumer product in the form of a solid detergent composition comprising:

- a solid detergent active base; preferably comprising at least one active material chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, the active base being used preferably in an amount comprised between 85 and 99.95% by weight based on the total weight of the composition, a microcapsule powder or microcapsule slurry as defined above, preferably in an amount comprised between 0.05 to 15 wt %, more preferably between 0.1 and 5 wt % by weight based on the total weight of the composition, optionally free perfume oil.

Shampoo/Shower Gel

An object of the invention is a consumer product in the form of a shampoo or a shower gel composition comprising:

a shampoo or a shower gel active base; preferably comprising at least one active material chosen in the group consisting of sodium alkylether sulfate, ammonium alkylether sulfates, alkylamphoacetate, cocamidopropyl betaine, cocamide MEA, alkylglucosides and aminoacid based surfactants and mixtures thereof, the active base being used preferably in an amount comprised between 85 and 99.95% by weight based on the total weight of the composition, a microcapsule slurry as defined above, preferably in an amount comprised between 0.05 to 15 wt %, more preferably between 0.1 and 5 wt % by weight based on the total weight of the composition, optionally free perfume oil.

Rinse-Off Conditioner

An object of the invention is a consumer product in the form of a rinse-off conditioner composition comprising:

a rinse-off conditioner active base; preferably comprising at least one active material chosen in the group consisting of cetyltrimonium chloride, stearyl trimonium chloride, benzalkonium chloride, behentrimonium chloride and mixture thereof, the active base being used preferably in an amount comprised between 85 and 99.95% by weight based on the total weight of the composition, a microcapsule slurry as defined above, preferably in an amount comprised between 0.05 to 15 wt %, more preferably between 0.1 and 5 wt % by weight based on the total weight of the composition, optionally free perfume oil.

Solid Scent Booster

An object of the invention is a consumer product in the form of a solid scent booster composition comprising:

a solid carrier, preferably chosen in the group consisting of urea, sodium chloride, sodium sulphate, sodium acetate, zeolite, sodium carbonate, sodium bicarbonate, clay, talc, calcium carbonate, magnesium sulfate, gypsum, calcium sulfate, magnesium oxide, zinc oxide, titanium dioxide, calcium chloride, potassium chloride, magnesium chloride, zinc chloride, saccharides such as sucrose, mono-, di-, and polysaccharides and derivatives such as starch, cellulose, methyl cellulose, ethyl cellulose, propyl cellulose, polyols/sugar alcohols such as sorbitol, maltitol, xylitol, erythritol, and isomalt, PEG, PVP, citric acid or any water soluble solid acid, fatty alcohols or fatty acids and mixtures thereof, a microcapsule slurry as defined above, in a powdered form, preferably in an amount comprised between 0.05 to 15 wt %, more preferably between 0.1 and 5 wt % by weight based on the total weight of the composition, optionally free perfume oil.

Liquid Scent Booster

An object of the invention is a consumer product in the form of a liquid scent booster composition comprising:

an aqueous phase, a surfactant system essentially consisting of one or more than one non-ionic surfactant, wherein the surfactant system has a mean HLB between 10 and 14, preferably chosen in the group consisting of ethoxylated aliphatic alcohols, POE/PPG (polyoxyethylene and polyoxypropylene) ethers, mono and polyglyceryl esters, sucrose ester compounds, polyoxyethylene hydroxylesters, alkyl polyglucosides, amine oxides and combinations thereof;

a linker chosen in the group consisting of alcohols, salts and esters of carboxylic acids, salts and esters of hydroxyl carboxylic acids, fatty acids, fatty acid salts, glycerol fatty acids, surfactant having an HLB less than 10 and mixtures thereof, and a microcapsule slurry as defined above, in the form of a slurry, preferably in an amount comprised between 0.05 to 15 wt %, more preferably between 0.1 and 5 wt % by weight based on the total weight of the composition, optionally free perfume oil.

Hair Coloration

An object of the invention is a consumer product in the form of an oxidative hair coloring composition comprising:

an oxidizing phase comprising an oxidizing agent and an alkaline phase comprising an alkaline agent, a dye precursor and a coupling compound; wherein said dye precursor and said coupling compound form an oxidative hair dye in the presence of the oxidizing agent, preferably in an amount comprised between 85 and 99.95% by weight based on the total weight of the composition, microcapsules as defined above, preferably in an amount comprised between 0.05 to 15 wt %, more preferably between 0.1 and 5 wt % by weight based on the total weight of the composition, optionally free perfume oil Perfuming Composition According to a particular embodiment, the consumer product is in the form of a perfuming composition comprising:

0.1 to 30%, preferably 0.1 to 20% of microcapsules as defined previously, 0 to 40%, preferably 3-40% of perfume, and 20-90%, preferably 40-90% of ethanol, by weight based on the total weight of the perfuming composition.

The invention will now be further described by way of examples. It will be appreciated that the invention as claimed is not intended to be limited in any way by these examples.

EXAMPLES

Example 1

Preparation of Cationic Polysuccinimide Derivatives

| Ingredients |
|---|
| Aspartic acid[1)] |
| Adipic acid[2)] |
| NaOH[3)] |
| Ethanolamine[4)] |
| EPTAC[5)] |

-continued

| Ingredients |
| --- |
| Cystamine[6) ]<br>DMAPA[7)]<br>DAM DPA[8)] |

[1)]Aspartic acid; origin: Sigma-Aldrich
[2)]Adipic acid, origin: Sigma-Aldrich
[3)]Sodium hydroxide, origin: Sigma-Aldrich
[4)]2-Aminoethanol, origin: Sigma-Aldrich
[5)]Glycidyltrimethylammonium chloride, origin: Sigma-Aldrich
[6)]Cystamine, origin: Sigma-Aldrich
[7)]N,N-Dimethyltrimethylenediamine, origin: Sigma-Aldrich
[8)]N,N-Bis(3-aminopropyl)methylamine, origin: Sigma-Aldrich

Example 1A: Preparation of PSI-co-DAMDPA-g-DMAPA-co-Mel in Solvent (Polysuccinimide Derivative A)

Preparation of Polysuccinimide (PSI Compound 1A):

Polysuccinimide was prepared in a steel autoclave reactor with aspartic acid (60 g) and phosporic acid (solution at 85% in water, 7 g). The solid was warmed up to 180° C. under vacuum for 6 h. The solid was purified by dissolving it in DMF followed by precipitation in water (step repeated two times) and then in methanol (two times) and filtration.

$^{1}$H-NMR (ppm, DMSO d-6, 400 MHz): 5.26, 4.55, 3.20, 2.70

FTIR (cm$^{-1}$): 2952, 1795, 1708

Preparation of PSI-co-DAMDPA-q-DMAPA Compound 2A:

PSI Compound 1A was dissolved in DMF at a concentration of 100 g/L. DAMDPA (0.04 eq.) and DMAPA (0.8 eq.) were added to the solution. The reaction mixture was stirred at 25° C. for 24 h. The copolymer was recovered by precipitation in diethyl ether, dried at 40° C. under vacuum for 24 h.

$^{1}$H-NMR (ppm, DMSO d-6, 400 MHz): 8.19, 5.05, 4.51, 3.68, 3.06, 2.12, 1.54

FTIR (cm$^{-1}$): 3291, 3060, 2941, 2863, 2817, 2775, 1711, 1644, 1528, 1464

Preparation of Cationic PSI-co-DAMDPA-q-DMAPA-co-Mel:

PSI-co-DAMDPA-g-DMAPA (Compound 2A 10 g) was dissolved in methanol (50 mL). Methyl iodide (17.5 g) (Mel) was added to the solution and the reaction mixture was stirred at 25° C. for 3 h. The solvent was evaporated at 50° C. under vacuum and the resulting solid was dried under vacuum for 24 h.

$^{1}$H-NMR (ppm, DMSO d-6, 400 MHz): 8.07, 4.56, 4.09, 3.61, 3.12, 2.73, 1.86, 1.23

Example 1B: Preparation of PSI-g-DMAPA-co-Mel (Polysuccinimide Derivative B)

Preparation of PSI-p-DMAPA Compound 1B:

PSI (Compound 1A) prepared in example 1 was added into a reactor. DMAPA (1 eq.) was added to the solid and intimately mixed to the polymer. The reaction mixture was stirred at 25° C. for 24 h and the resulting solid was dried at 40° C. under vacuum for 24 h.

$^{1}$H-NMR (ppm, DMSO d-6, 400 MHz): 8.29, 5.28, 4.52, 3.72, 3.06, 2.75, 2.10, 1.59, 1.53

FTIR (cm$^{-1}$): 3287, 3059, 2941, 2861, 2816, 2773, 1642, 1529, 1463

Preparation of PSI-p-DMAPA-co-Mel:

PSI-g-DMAPA (Compound 1B 10 g) was dissolved in methanol (50 mL). Methyl iodide (17.5 g) was added to the solution and the reaction mixture was stirred at 25° C. for 3 h. The solvent was evaporated at 50° C. under vacuum and the resulting solid was dried under vacuum for 24 h.

$^{1}$H-NMR (ppm, DMSO d-6, 400 MHz): 8.05, 5.21, 4.55, 3.12, 1.86, 1.23

Example 1C: Preparation of PSI-co-AD-g-DMAPA-co-Mel Based on Reactive Extrusion (Polysuccinimide Derivative C)

Preparation of PSI-co-AD Compound 1C:

Aspartic acid (15 eq.) and adipic acid (1 eq.) were mixed together and added to the extruder Leistritz LD40. Feed rate was 600 g/h and screw speed at 300 rpm under argon. Temperatures of the eight sections were 80, 180, 250, 250, 240, 230, 220 and 220° C. from section 1 (feeding) to section 8 (outlet). No die was used and no further purification was carried out on the solid.

$^{1}$H-NMR (ppm, DMSO d-6, 400 MHz): 11.62, 8.59, 5.26, 5.17, 4.59, 3.19, 2.71, 2.20, 2.11, 1.48

FTIR (cm$^{-1}$): 2949, 1793, 1703, 1528

Preparation of PSI-co-AD-q-DMAPA Compound 2C

PSI-co-AD Compound 1C was added into a reactor. DMAPA (0.8 eq.) was added to the solid and intimately mixed to the polymer. The reaction mixture was stirred at 25° C. for 24 h and the resulting solid was dried at 40° C. under vacuum for 24 h.

$^{1}$H-NMR (ppm, DMSO d-6, 400 MHz): 7.95, 6.84, 5.25, 5.15, 4.46, 3.04, 2.17, 2.11, 2.09, 1.60, 1.51

FTIR (cm$^{-1}$): 3291, 2942, 2861, 2816, 2767, 1643, 1535, 1460

Preparation of PSI-co-AD-q-DMAPA-co-Mel:

PSI-co-AD-g-DMAPA (Compound 2C 10 g) was dissolved in methanol (50 mL). Methyl iodide (35 g) was added to the solution and the reaction mixture was stirred at 25° C. for 3 h. The solvent was evaporated at 50° C. under vacuum and the resulting solid was dried under vacuum for 24 h.

$^{1}$H-NMR (ppm, DMSO d-6, 400 MHz): 8.03, 5.26, 4.51, 3.09, 2.63, 2.18, 1.84, 1.45

FTIR (cm$^{-1}$): 3262, 3010, 2946, 1708, 1654, 1648, 1523, 1476, 1438

Example 2

Preparation of Coated Microcapsules

Microcapsules A preparation

In a round bottom flask, melamine (0.8 g), 2,2-dimethoxyethanal (60 wt % in water, 1.22 g), glyoxal (40 wt % in water, 1.54 g) and 2-oxoacetic acid (50 wt % in water, 0.52 g) were dispersed in water (2.06 g) at RT. The pH value of the dispersion was controlled with sodium hydroxide (30 wt % in water, 0.86 g, pH=9.5). The reaction mixture was heated at 45° C. for 25 minutes to give a solution. Then water (6.72 g) was added and the resin was stirred at 45° C. until fully transparent.

Resin was transferred in a 200 mL beaker. Guanazole (0.55 g) was dissolved in a solution of Ambergum 1221 (2 wt % in water, 25.18 g). The resulting solution was introduced into the beaker. An oil solution of Takenate D-110N (1.94 g) and a perfume oil (24.97 g—see Table 1) was added into the aqueous solution. The biphasic reaction mixture was sheared with an Ultra-turrax at 24000 rpm for 2 min. Acetic acid (0.14 g) was added to initiate the polycondensation (pH=5.35). The quality of the emulsion was controlled by light microscopy. The emulsion was transferred into a 200 mL Schmizo reactor and was heated at 45° C. for 1 h, then at 60° C. for 1 h and finally at 80° C. for 30 minutes and colled to 70° C. over 25 min to obtain a microcapsule slurry.

The polysuccinimide polymer is solubilized in water and then an appropriate amount of the microcapsule slurry and the polysuccinimide polymer solution are weighted as to obtain a final polymer loading of 0.7% in the slurry. The slurry is initially heated at 70° C., then the polymer added and the mixture is kept at 70° C. under stirring for 1 hour.

TABLE 1

Perfume oil composition

| RAW MATERIAL | QTY (G) |
|---|---|
| CARBINOL ACETATE | 2.2 |
| CITRONELLYL ACETATE | 16.59 |
| LINALYL ACETATE | 10.72 |
| NOPYLE ACETATE | 7.97 |
| TERPINYL ACETATE | 2.11 |
| VERDYL ACETATE | 2.89 |
| DECANAL | 0.07 |
| HEXYLCINNAMIC ALDEHYDE | 13.94 |
| (+−)-ETHYL 2-METHYLPENTANOATE | 0.26 |
| BENZYL BENZOATE | 8.19 |
| CYCLOGALBANATE | 2.14 |
| (+−)-METHYL (3-OXO-4-PENTYLCYCLOPENTYL)ACETATE | 11.94 |
| HEXYL ISOBUTYRATE | 2.63 |
| 2-(2-(4-METHYL-3-CYCLOHEXEN-1-YL)PROPYL)CYCLOPENTANONE | 10.34 |
| OXANE | 0.08 |
| (2RS,4SR)-4-METHYL-2-(2-METHYL-l-PROPEN-1-YL)TETRAHYDRO-2H-PYRAN (A) + (2RS,4RS)-4-METHYL-2-(2-METHYL-l-PROPEN-1-YL)TETRAHYDRO-2H-PYRAN (B) | 0.44 |
| VERDYL PROPIONATE | 4.33 |
| (3E)-4-(2,6,6-TRIMETHYL-l-CYCLOHEXEN-l-YL)-3-BUTEN-2-ONE | 0.52 |
| (3Z)-3-HEXEN-l-YL (3Z)-3-HEXENOATE | 1.24 |
| (1RS,2SR)-2,4-DIMETHYL-3-CYCLOHEXENE-1-CARBALDEHYDE | 1.42 |

TABLE 2

Microcapsule slurry composition

| capsule | polymer | mass of initial mg slurry (g) | mass of polymer solution (g) | polymer loading | % oil in final formulation |
|---|---|---|---|---|---|
| Capsules A + Polysuccinimide derivative C | Polysuccinimide derivative C 14 wt % solution | 5.68 | 0.29 | 0.7% | 35.68% |
| Capsules A + Polysuccinimide derivative A | Polysuccinimide derivative A 3 wt % solution | 7.68 | 2.3 | 0.7% | 28.86% |
| Capsules A + Polysuccinimide derivative B | Polysuccinimide derivative B 3 wt % solution | 7.64 | 2.5 | 0.7% | 28.25% |

Example 3

Characterization of the Coated Microcapsules

Z Potential

The Z potential of the capsules before and after coating has been measured by means of a Malvern Zetasizer Nano, by diluting the slurry in a 1 mM NaCl solution. The coated capsules have then been washed three times by centrifugation (2-3 ml of slurry diluted in 30 ml of water, centrifuged 15 min at 4000 RPM, surnatant eliminated and the residual solid redispersed in 30 ml of DI water) and the Z potential re-measured as to test whether it was desorbed or not. The results are visible in the Table below.

TABLE 3

Zeta potential

| | Zeta Potential (mV) |
|---|---|
| Capsules A coated with polysuccinimide derivative C | −53.6 |
| Capsules A coated with Polysuccinimide derivative A | −71 |
| Capsules A coated with Polysuccinimide derivative B | −49.4 |

Example 4

Performance of Coated Microcapsules in a Shampoo

Deposition of microcapsules according to the invention was measured from rinse-off shampoo (see table below)

TABLE 4

Hair shampoo base formulation

| Ingredient | Percentage |
|---|---|
| Water | 45 |
| Sodium Laureth Sulfate | 32 |
| Sodium Chloride (10% aqueous | 15 |

TABLE 4-continued

| Hair shampoo base formulation | |
|---|---|
| Ingredient | Percentage |
| solution) | |
| Cocamidopropyl Betaine | 3.2 |
| Disodium Cocoamphodiacetate | 2 |
| Glycerin 85% | 1 |
| Polyquaternium 10 | 0.3 |
| Glyceryl Laurate | 0.3 |
| DMDM Hydantoin | 0.2 |
| Sodium Methylparaben | 0.1 |
| Citric Acid (10% aqueous solution) | q.s. |

Deposition Testing:

For the quantification of deposition, the following procedure was used. A 500 mg mini brown Caucasian hair swatch was wet with 40 mL of tap water (39° C.) aimed at the mount with a 140 mL syringe. The excess water was gently squeezed out once and 0.1 mL of a model surfactant mixture containing microcapsules loaded with a UV tracer (Uvinul A Plus) was applied with a 100 μL positive displacement pipet. The surfactant mixture was distributed with 10 horizontal and 10 vertical passes. The swatch was then rinsed with 100 mL of tap water (39° C.) with 50 mL applied to each side of the swatch aimed at the mount. The excess water was gently squeezed out and the hair swatch was then cut into a pre-weighed 20 mL scintillation vial. This process was repeated in triplicate and then the vials containing the cut hair were dried in a vacuum oven at 50-60° C. (100 Torr) for at least 5 hours. After the drying process, the vials were again weighed to determine the mass of the hair in the vials. Controls were also prepared by adding 0.1 mL of a model surfactant mixture containing microcapsules to an empty vial. 4 mL of 200 proof ethanol were then added to each vial and they were subjected to 60 min of sonication. After sonication, the samples were filtered through a 0.45 μm PTFE filter and analysed with a HPLC using a UV detector. To determine the percentage of deposition of microcapsules from a model surfactant mixture, the amount of Uvinul extracted from the hair samples was compared to the amount of Uvinul extracted from the control samples.

TABLE 5

| Deposition | |
|---|---|
| Sample | Deposition % |
| Capsules A coated with polysuccinimide derivative C- 0.7% | 2.8 |

This result shows that the capsules of the invention have a good deposition.

Example 5

Fabric Softener Composition

Microcapsules A of the present invention are dispersed in a fabric softener composition (see below) to obtain a concentration of encapsulated perfume oil at 0.22%.

TABLE 6

| Fabric Conditioner composition | |
|---|---|
| Product | Wt % |
| Stepantex VL 90A | 8.88 |
| Calcium Chloride Sol. 10% | 0.36 |
| Proxel GXL | 0.04 |
| Perfume | 1 |
| Water | 89.72 |
| TOTAL | 100 |

Example 6

Liquid Detergent Composition

Microcapsules A of the present invention are dispersed in a liquid detergent base (see below) to obtain a concentration of encapsulated perfume oil at 0.22%.

TABLE 7

| Liquid detergent composition | |
|---|---|
| Ingredients | Concentration [wt %] |
| Sodium C14-17 Alkyl Sec Sulfonate[1)] | 7 |
| Fatty acids, C12-18 and C18-unsaturated[2)] | 7.5 |
| C12/14 fatty alcohol polyglycol ether with 7 mol EO[3)] | 17 |
| Triethanolamine | 7.5 |
| Propylene Glycol | 11 |
| Citric acid | 6.5 |
| Potassium Hydroxyde | 9.5 |
| Protease | 0.2 |
| Amylase | 0.2 |
| Mannanase | 0.2 |
| Acrylates/Steareth-20 Methacrylate structuring Crosspolymer[4)] | 6 |
| Deionized Water | 27.4 |

[1)]Hostapur SAS 60; Origin: Clariant
[2)]Edenor K 12-18; Origin: Cognis
[3)]Genapol LA 070; Origin: Clariant
[4)]Aculyn 88; Origin: Dow Chemical

Example 7

Rinse-Off Conditioner

Microcapsules A of the present invention are dispersed in a rinse-off conditioner base (see below) to obtain a concentration of encapsulated perfume oil at 0.5%.

TABLE 8

| Rinse-off conditioner composition | | |
|---|---|---|
| | Ingredients | Concentration [wt %] |
| A | Water deionized | 81.8 |
| | Behentrimonium Chloride[1)] | 2.5 |
| | Hydroxyethylcellulose[2)] | 1.5 |
| B | Cetearyl Alcohol[3)] | 4 |
| | Glyceryl Stearate (and) PEG-100 Stearate[4)] | 2 |
| | Behentrimonium Methosulfate (and) Cetyl alcohol (and) Butylene Glycol[5)] | 4 |
| | Ethoxy (20) Stearyl Alcohol[6)] | 1 |

TABLE 8-continued

Rinse-off conditioner composition

| | Ingredients | Concentration [wt %] |
|---|---|---|
| C | Amodimethicone (and) Trideceth-12 (and) Cetrimonium Chloride[7] | 3 |
| | Chlorhexidine Digluconate[8] 20% aqueous solution | 0.2 |
| D | Citric acid 10% aqueous sol. till pH 3.5-4 | q.s. |
| | TOTAL: | 100 |

[1]Genamin KDM P, Clariant
[2]Tylose H10YG4, Shin Etsu
[3]Lanette 0, BASF
[4]Arlacel 165-FP-MBAL-PA-(RB), Croda
[5]Incroquat Behenyl TMS-50-MBAL-PA-(MH) HA4112, Croda
[6]SP Brij S20 MBAL-PA(RB), Croda
[7]Xiameter DC MEM-0949 Emulsion, Dow Corning
[8]Alfa Aesar

Example 8

Shampoo Composition

Microcapsules A of the present invention are weighed and mixed in a shampoo composition (see below) to add the equivalent of 0.2% perfume.

TABLE 9

Shampoo composition

| | Ingredients | Concentration [wt%] |
|---|---|---|
| A | Water deionized | 44.4 |
| | Polyquaternium-10[1] | 0.3 |
| | Glycerin 85%[2] | 1 |
| | DMDM Hydantoin[3] | 0.2 |
| B | Sodium Laureth Sulfate[4] | 28 |
| | Cocamidopropyl Betaine[5] | 3.2 |
| | Disodium Cocoamphodiacetate[6] | 4 |
| | Ethoxy (20) Stearyl Alcohol[6] | 1 |
| C | Sodium Laureth Sulfate[4] | 3 |
| | Glyceryl Laureate[7] | 0.2 |
| D | Water deionized | 1 |
| | Sodium Methylparaben[8] | 0.1 |
| E | Sodium Chloride 10% aqueous sol. | 15 |
| | Citric acid 10% aqueous sol. till pH 5.5-6 | q.s. |
| | Perfume | 0.5 |
| | TOTAL: | 100 |

[1]Ucare Polymer JR-400, Noveon
[2]Schweizerhall
[3]Glydant, Lonza
[4]Texapon NSO IS, Cognis
[5]Tego Betain F 50, Evonik
[6]Amphotensid GB 2009, Zschimmer & Schwarz
[7]Monomuls 90 L-12, Gruenau
[8]Nipagin Monosodium, NIPA

Example 9

Antiperspirant Roll-on Emulsion Composition

Microcapsules A of the present invention are weighed and mixed in antiperspirant roll-on emulsion composition (see below) to add the equivalent of 0.2% perfume.

TABLE 10

Antiperspirant composition

| Ingredient | Amount (wt %) |
|---|---|
| Steareth-2[1] (Part A) | 3.25 |
| Steareth-21[2] (Part A) | 0.75 |
| PPG-15 Stearyl Ether[3] (Part A) | 4 |
| WATER deionised (Part B) | 51 |
| Aluminum Chlorohydrate 50% aqueous solution[4] (Part C) | 40 |
| Fragrance (Part D) | 1 |

[1]BRU 72; origin: ICI
[2]BRU 721; origin: ICI
[3]ARLAMOL E; origin: UNIQEMA-CRODA
[4]LOCRON L; origin: CLARIAN Part A and B are heated separately to 75° C.; Part A is added to Part B under stirring and the mixture is homogenized for 10 min. Then, the mixture is cooled under stirring; and Part C is slowly added when the mixture reached 45° C. and Part D when the mixture reached at 35° C. while stirring. Then the mixture is cooled to room temperature.

Example 10

Shower-Gel Composition

Microcapsules A- of the present invention are weighed and mixed in the following composition to add the equivalent of 0.2% perfume.

TABLE 11

Shower gel composition

| Ingredients | Amount (% wt) | Function |
|---|---|---|
| WATER deionized | 49.350 | Solvent |
| Tetrasodium EDTA[1] | 0.050 | Chelating agent |
| Acrylates Copolymer[2] | 6.000 | Thickener |
| Sodium C12-C15 Pareth Sulfate[3] | 35.000 | Surfactant |
| Sodium Hydroxide 20% aqueous solution | 1.000 | pH adjuster |
| Cocamidopropyl Betaine[4] | 8.000 | Surfactant |
| Methylchloroisothiazolinone and Methylisothiazolinone[5] | 0.100 | Preservative |
| Citric Acid (40%) | 0.500 | pH adjuster |

[9]EDETA B POWDER; trademark and origin: BASF
[10]CARBOPOL AQUA SF-1 POLYMER; trademark and origin: NOVEON
[11]ZETESOL AO 328 U; trademark and origin: ZSCHIMMER & SCHWARZ
[12]TEGO-BETAIN F 50; trademark and origin: GOLDSCHMIDT
[13]KATHON CG; trademark and origin: ROHM & HASS

What is claimed is:

1. A core-shell microcapsule slurry comprising at least one microcapsule having
a) an oil-based core comprising a hydrophobic material;
b) a polymeric shell; and
c) a coating comprising a polysuccinimide derivative, wherein the polysuccinimide derivative is obtained by grafting at least two amines to at least one succinimide repeating unit, wherein the two amines are N,N-Dimethyltrimethylenediamine (DMAPA) and N,N-Bis(3-aminopropyl)methylamine (DAMDPA).

2. The microcapsule slurry according to claim 1, wherein the molar ratio between N,N-Bis(3-aminopropyl)methylamine (DAMDPA) and the polysuccinimide unit is between 0.1 to 0.01 and wherein the molar ratio between N,N-Dimethyltrimethylenediamine (DMAPA) and the polysuccinimide unit is between 1 to 0.01.

3. The microcapsule slurry according to claim 1, wherein the polymeric shell comprises a material selected from the group consisting of polyurea, polyurethane, polyamide, polyester, polyacrylate, polysiloxane, polycarbonate, polysulfonamide, polymers of urea and formaldehyde, polymers of melamine and formaldehyde, polymers of melamine and urea, polymers of melamine and glyoxal, and mixtures thereof.

4. The microcapsule slurry according to claim 1, wherein the oil-based core comprises a perfume oil.

5. A process for preparing the microcapsule slurry according to claim 1, the process comprising the steps of:

a) preparing an oil phase comprising the hydrophobic material to form the oil phase;

b) preparing an aqueous solution comprising optionally an emulsifier to form a water phase;

c) adding the oil phase to the water phase to form an oil-in-water dispersion;

d) adding a polyfunctional monomer in the oil phase and/or the water phase;

e) performing a curing step to form core-shell microcapsule in the form of a slurry; and f) adding a polysuccinimide derivative in step d) or after step d) is completed;

wherein the polysuccinimide derivative is obtained by grafting at least two amines to at least one succinimide repeating unit, wherein the two amines are N,N-Dimethyltrimethylenediamine (DMAPA) and N,N-Bis(3-aminopropyl)methylamine (DAMDPA).

6. A consumer product comprising:

a consumer product base, and the microcapsule slurry according to claim 1.

7. The consumer product according to claim 6, wherein the consumer product is a perfumed consumer product selected from the list consisting of a fine perfume, a splash perfume, an eau de perfume, a cologne, a shave lotion, an after-shave lotion, a liquid detergent, a solid detergent, a mono chamber unidose detergent, a multi chamber unidose detergent, a fabric softener, a fabric refresher, liquid scent-boosters, solid scent-boosters, a dryer sheet, an ironing water, a paper, a bleach, carpet cleaners, curtain-care products, a shampoo, a coloring preparation, a color care product, a hair shaping product, a dental care product, a disinfectant, an intimate care product, a hair spray, a hair conditioning product, a vanishing cream, a deodorant, an antiperspirant, hair remover, a tanning product, a sun product, nail products, skin cleansing, a makeup, a perfumed soap, shower mousse, shower oil, shower gel, bath mousse, bath oil, bath gel, foot/hand care products, a hygiene product, an air freshener, a powdered air freshener, a mold remover, furnisher care, wipe, a dish detergent, a hard-surface detergent, a leather care product, and a car care product.

8. A perfumed consumer product according to claim 7, wherein the perfumed consumer product is a liquid or solid detergent, a fabric softener, liquid or solid scent-boosters, a shampoo, a shower gel, a hair conditioning product, a deodorant or antiperspirant.

9. The microcapsule slurry according to claim 2:

wherein the polymeric shell comprises a material selected from the group consisting of polyurea, polyurethane, polyamide, polyester, polyacrylate, polysiloxane, polycarbonate, polysulfonamide, polymers of urea and formaldehyde, polymers of melamine and formaldehyde, polymers of melamine and urea, polymers of melamine and glyoxal and mixtures thereof; and wherein the oil-based core comprises a perfume oil.

10. The consumer product of claim 6, wherein the consumer product is in the form of a home-care product or a personal care product.

* * * * *